United States Patent [19]

Corley

[11] Patent Number: 4,898,999

[45] Date of Patent: Feb. 6, 1990

[54] PROCESS FOR HALOGENATING CYCLOBUTENOARENES

[75] Inventor: Larry S. Corley, Houston, Tex.

[73] Assignee: Shell Oil Company, Houston, Tex.

[21] Appl. No.: 201,818

[22] Filed: Jun. 3, 1988

[51] Int. Cl.$^4$ .................. C07C 17/12; C07C 17/04
[52] U.S. Cl. ..................................... 570/207; 570/206
[58] Field of Search .............................. 570/206, 207

[56] References Cited

U.S. PATENT DOCUMENTS

| | | | |
|---|---|---|---|
| 3,940,434 | 2/1976 | Haas et al. | 260/475 SC |
| 4,540,763 | 9/1985 | Kirchhoff | 526/281 |
| 4,570,011 | 2/1986 | So | 560/8 |
| 4,590,304 | 5/1986 | Wallace et al. | 568/766 |
| 4,622,375 | 11/1986 | Wong | 526/284 |
| 4,638,078 | 1/1987 | Kirchhoff | 558/414 |
| 4,642,329 | 2/1987 | Kirchhoff et al. | 526/284 |
| 4,667,004 | 5/1987 | Wong | 526/284 |
| 4,667,005 | 5/1987 | Wong | 526/284 |
| 4,822,930 | 4/1989 | Liu | 570/206 |

FOREIGN PATENT DOCUMENTS 672630  5/1952  United Kingdom ................ 570/207

OTHER PUBLICATIONS

Lloyd & Ongley, *Tetrahedron* 21, 245–254 (1965).

*Primary Examiner*—Warren B. Lone

[57] ABSTRACT

A process for the preparation of cyclobutenohaloarenes is described in which a cyclobutenoarene such as benzocyclobutene is reacted with a halogen in the organic phase of a two-phase organic/aqueous system to form a cyclobutenohaloarene and hydrogen halide, the latter which migrates into the aqueous phase. The process has the advantages of low acidity of the reaction phase, and the consequent reduced side halogenation product formation and necessity for the introduction of caustic in the recovery step, and relatively simple recovery of the cyclobutenohaloarene from the reaction mixture.

18 Claims, No Drawings

PROCESS FOR HALOGENATING CYCLOBUTENOARENES

BACKGROUND OF THE INVENTION

This invention relates to a process for preparing halogenated cyclobutenoarenes. In a specific aspect, the invention relates to a simple, low-temperature process for preparing 4-halobenzocyclobutenes in good yields without the side production of large quantities of chemical by-products and waste.

The four-membered ring of benzocyclobutenes is known to open at elevated temperature to form a very reactive diene which rapidly dimerizes and polymerizes. Molecules containing two or more benzocyclobutene groups are therefore useful as heat-curable thermosetting resins. Also, elastomers or thermoplastics containing benzocyclobutene substituents crosslink on heating. Among the more useful intermediates for preparing benzocyclobutene resins or benzocyclobutene-functionalized elastomers or thermoplastics are the 3- or 4-halobenzocyclobutenes, which undergo the many reactions of aromatic halides such as Grignard and Ullmann reactions.

However, the preparation of such halobenzocyclobutene starting materials poses a number of practical problems. Under the usual conditions of halogenation of the benzene ring, opening of the four-membered ring of the benzocyclobutene molecule tends to compete strongly with substitution on the aromatic ring. The ring-opening side reaction is a particularly significant problem under conditions of high acidity and high temperature, as are conventionally used in processes for the halogenation of aromatic hydrocarbons using, for example, a ferric bromide or ferric chloride catalyst.

It is possible, as illustrated in Example 6 of U.S. Pat. No. 4,540,763, to obtain reasonable yields of 4-halobenzocyclobutenes under relatively mild reaction conditions. As described therein, 4-bromobenzocyclobutene can be prepared by the bromination of benzocyclobutene for four days with a large excess of pyridinium bromide perbromide, catalyzed by mercuric acetate. A relatively good yield of isolated product (66%) was obtained. However, the long reaction time, the toxicity of mercury and the large quantity of waste pyridine (and waste HBr, from which the pyridine must be freed by alkali neutralization) are major disadvantages of this procedure.

A somewhat simpler procedure for brominating benzocyclobutene has been published in *Tetrahedron*, 21, 245-254 (1965). This procedure uses elemental bromine in 95% aqueous acetic acid with an iodine catalyst. A 78% yield was obtained from a synthesis using less than 5 grams of starting material. However, commercial use of such a process would be uneconomical because the amount of acetic acid used is more than ten times the amount of benzocyclobutene starting material used. The acetic acid keeps the product bromobenzocyclobutene, by-product HBr and side products in one phase throughout the reaction. Attempted distillation of the product mixture to remove acetic acid and HBr would require elevated temperatures, which would have the undesirable effect of promoting the opening of the benzocyclobutene ring by the HBr, thus consuming the product. Low-temperature isolation of the product would require extraction of the acetic acid into a basic aqueous solution, which would require large quantities of alkali and would produce large amounts of waste from which recovery of the acetic acid and HBr would be expensive.

It is therefore an object of the invention to provide a process for the preparation of cyclobutenohaloarenes. In one embodiment, it is an object of the invention to prepare halogenated benzocyclobutenes in a low-temperature process which produces relatively small quantities of waste by-products and does not require an acid medium for the halogenation reaction.

SUMMARY OF THE INVENTION

According to the invention, an aromatic ring of a cyclobutenoarene is halogenated in a process which involves the reaction of the cyclobutenoarene and a halogen in an organic phase of a reaction mixture which also includes an aqueous phase. The aqueous phase can be water alone or a water solution of other reaction-promoting materials such as buffers. As the halogen and cyclobutenoarene are reacted to form a cyclobutenohaloarene, by-product HX migrates into the aqueous phase. The reaction can if desired be carried out at relatively mild temperatures, generally about 0° C. to about room temperature. Upon completion of the reaction, the product mixture includes an organic phase containing cyclobutenohaloarene and side products and an aqueous phase containing HX in solution. The acid can be mechanically separated from the organic layer and recovered without neutralization. The organic layer can be washed and dried and the cyclobutenohaloarene purified by distillation, chromatography or other suitable method.

DETAILED DESCRIPTION OF THE INVENTION

The invention process involves the reaction of a cyclobutenoarene containing one or more aromatic rings with a halogen in the organic phase of a reaction mixture which also includes an aqueous phase. The cyclobutenoarene starting material is most commonly benzocyclobutene or a substituted derivative thereof, such as a benzocyclobutene containing alkyl, halo or other substituents. Such benzocyclobutenes include aromatic compounds which can be represented by the general formula

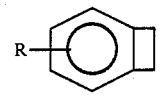

in which each R is selected independently from substituents which are not destroyed by halogen or water, including for example halide and $C_{1-4}$ alkyl. As used herein, "benzocyclobutenes" shall mean cyclobutenoarenes and substituted derivatives thereof.

The reaction mixture includes a halogen source. The halogen source may be introduced into the reaction vessel in the form of halogen molecules $X_2$, wherein X is chlorine, bromine or iodine, or it may be generated in the reaction vessel from reactants added to the reaction mixture. For example, in the bromination of benzocyclobutenes, bromine as $Br_2$ may be introduced into the reaction mixture or, alternatively, bromine can be generated in situ from the reaction of aqueous hydrobromic acid and an oxidizing agent such as sodium chlorate. The amount of $X_2$ present in the reaction mixture will generally be within the range of about 0.5 to about 1.5 moles, usually about 0.8 to about 1.2 moles per mole of benzocyclobutene.

The reaction mixture includes an aqueous phase, which can be water or a water solution containing reaction-assisting materials. The aqueous phase may contain, for example, buffers such as sodium phosphates and sodium sulfates, acids such as sulfuric acid to promote the in situ production of $X_2$, and reactants for the in situ production of $X_2$ or a catalyst, for example. The amount of water can vary widely depending upon the choice of other reaction variables, but will generally be within the weight ratio range of from about 0.1:1 to about 10:1 (water:benzocyclobutene starting material), preferably from about 0.3:1 to about 3:1, most preferably from about 0.5:1 to about 1.5:1.

The halogenation process is carried out by contacting, in the organic phase, the benzocyclobutene and the halogen under reaction conditions suitable for electrophilic aromatic substitution, generally atmospheric pressure at a temperature within the range of about −80° C. to 80° C. Temperatures within the upper portion of this range can be employed so long as competing reactions of the halogen with the cyclobutene side ring do not result in an unacceptable level of side products. The reaction can generally be carried out at atmospheric pressure under relatively mild temperatures, such as −20° C. to 30° C., preferably about −10° C. to about 20° C. Added pressure may be desirable under certain reaction conditions, as where the halogen is $Cl_2$, for example. The invention process provides a method for minimizing the amount of undesirable acid in the halogenation reaction medium, and it is contemplated that, with the exception of HX byproduct, the organic phase be essentially acid-free. The time over which the reaction conditions will be maintained can vary widely depending upon the reaction conditions, but will generally be within the range of about 1 to about 24 hours, usually about 2 to about 18 hours.

As the halogenation reaction proceeds, HX is formed and migrates into the aqueous phase in the reaction mixture. After completion of the reaction, the reaction mixture includes an organic phase containing 4-halobenzocyclobutene and side products and an aqueous phase which includes HX in solution, the HX concentration being determined by the amount of water in the aqueous phase, e.g., the amount in the initial reaction mixture plus any amounts added during the course of the reaction. The aqueous phase and organic phase can be separated by mechanical means, such as centrifugation and draining the organic phase from the bottom of the reaction vessel, for example.

Side products which can be produced during the halogenation reaction include isomers of 4-halobenzocyclobutene such as 3-halobenzocyclobutene and dihalides such as 1-halo-2-(2-haloethyl)benzene. Such side products can be removed from the organic phase by distillation or reflux with an amine, for example.

The process is effective in producing high yields of 4-halobenzocyclobutene, on the order of at least about 60%, preferably about 75%, based on benzocyclobutene starting material, under relatively mild reaction conditions, but yields in a particular case will of course vary depending upon the reactants and reaction conditions employed.

The halogenation reaction can optionally be carried out in the presence of a suitable catalyst, such as iodine, but reaction rates have generally not been found to be sufficiently improved to justify the cost of an iodine catalyst.

The process has the advantage of minimizing the acidity of the reaction product medium (the organic phase of the two-phase system), thereby reducing the production of halogenated side products which result from acid-induced ring opening. Low acidity in the reaction phase is made possible by the absence of an acid reaction solvent and by migration of the HX from the organic reaction phase into the aqueous phase.

EXAMPLE 1

This example describes, for comparison purposes, halogenation of benzocyclobutene by a process similar to that of Lloyd and Ongley, Tetrahedron 21, 245–254 (1965). (The benzocyclobutene reactant contained 3% styrene and 2% o-xylene by $^{13}C$ NMR analysis.) 20.8 grams (0.2 mole) of benzocyclobutene (BCB) were added to a mixture of 152 grams of acetic acid, 8 grams of water and 0.61 grams of potassium iodide (source of iodine catalyst) in a flask with a magnetic stirrer. The resulting solution was homogeneous. The BCB solution was cooled to below 5° C. with an ice bath. A mixture of 35.2 grams of bromine and 22 grams of acetic acid was placed in an addition funnel and added dropwise to the BCB solution, at an addition rate such that the temperature of the BCB solution did not rise above 5° C. The mixture was then held below 5 C. for 24 hours, at the end of which time much of the acetic acid had crystallized. (the mixture still had the dark red color of unreacted bromine.) The acetic acid was then brought into solution by addition of approximately 50 mL of water to the mixture. This melted mixture was then poured into a 1-liter separatory funnel.

To the funnel were added 100 mL of 1,1,1-trichloroethane, approximately 160 mL of 50% aqueous NaOH, and an unmeasured quantity of ice. The mixture was shaken until the bromine color was discharged. The organic layer was then separated, dried over calcium oxide, and analyzed by gas chromatography on a packed column of Chromosorb 101. The chromatogram contained three major peaks in addition to solvent. The first peak corresponded to unreacted benzocyclobutene, the second to the desired product (4-bromobenzocyclobutene) and the third to a mixture of side products believed to consist largely of 1-bromo-2-(2-bromoethyl)benzene. The starting material peak area comprised 26.6% of the total area for all peaks other than the solvent peak. The area of the peak corresponding to the desired product comprised 58.5% of the total area of all product peaks (not including solvent and starting material).

EXAMPLE 2

This example demonstrates the bromination of benzocyclobutene (from the same batch of BCB used in Example 1) in a heterogeneous reaction mixture containing an aqueous phase. Benzocyclobutene (10.4 grams, 0.1 mole) and 10.4 grams of water were combined in a 100-mL flask equipped with a magnetic stirrer. The mixture was cooled to 5° C. in an ice bath. An addition funnel containing 17.6 grams (0.1 mole) of bromine was attached to the flask. The bromine was added to the benzocyclobutene mixture dropwise over a period of about 30 minutes, such that the temperature of the reaction mixture did not rise above approximately 15° C. during the bromine addition. The ice bath was then removed while stirring was continued. The temperature of the reaction mixture rose to 27° C. and stabilized at this level. The reaction mixture was then poured from the flask into a 50-mL bottle which was capped and then tumbled overnight at room temperature.

Approximately 16 hours later, the bromine color had become very faint. Approximately 2 mL of a 7% aqueous solution of $NaHSO_3$ was added to the bottle; subsequent shaking completely discharged the bromine color. The mixture was poured into a 100-mL separatory funnel. The lower (organic) layer was separated and dried over calcium oxide. Approximately 19 grams of organic layer were isolated. The dried organic layer was analyzed by gas chromatography on a column of Chromosorb 101. The chromatogram contained 4 major peaks. The first peak (unreacted benzocyclobutene) comprised only 2% of total peak area. The second peak (the desired 4-benzocyclobutene product) comprised 77% of total peak area, the rest being made up by a major and minor side product peak. The identity of the major component was confirmed by $^{13}C$ NMR spectroscopy.

EXAMPLE 3

This example illustrates the preparation of 4-halobenzocyclobutenes in an aqueous system in which the halogen is generated in situ within the reaction vessel. A 5-liter 3-neck round bottom flask was charged with 884 grams (8.5 moles) of benzocyclobutene (98.4% pure by capillary gas chromatography, containing 1.4% of o-xylene and 0.2% of other impurities) and 1581 grams (9.38 moles) of 48% aqueous hydrobromic acid. The flask was then fitted with a paddle stirrer, thermometer and dropping funnel. The dropping funnel was charged with a solution of 301.8 grams (2.83 moles) of sodium chlorate in 595 grams of water. The mixture in the flask was cooled to below 0° C. with a dry ice/acetone bath.

The solution of sodium chlorate in water was then added from the dropping funnel at a rate such that the temperature of the flask contents stayed below 0° C. The dropping funnel was then charged with 833 grams (8.5 moles) of concentrated sulfuric acid. The sulfuric acid was then added to the flask at the rate such that the temperature of the flask contents stayed generally below 0° C. (although one excursion to 12° C. occurred near the end of the acid addition). The temperature was then allowed to drop to −15° C. after the end of the acid addition. The dry ice bath was then removed and the temperature of the reaction mixture was allowed to rise to 0° C. An ice-water cooling bath was then placed around the flask. The temperature of the reaction mixture rose to 8° C. to 12° C. over a period of about 30 minutes with ice-bath cooling. Ice-bath cooling was maintained for approximately 3 hours and the ice was then allowed to melt overnight as the reaction was completed (still under stirring).

The following morning, the mixture was decolorized with approximately 850 grams of a 20% aqueous solution of $NaHSO_3$. The organic layer was found by capillary GC (Supelco SPB-5 mobile phase) to contain 71.5% of 4-bromobenzocyclobutene, 11.3% of 1-bromo-2-(2-bromoethyl)benzene, 10.3% of unreacted benzocyclobutene starting material, 1.2% of 4-bromo-o-xylene, 1.0% of 3-bromobenzocyclobutene, 0.2% of 4-chlorobenzocyclobutene and 0.2% of unreacted o-xylene (impurity in the benzocyclobutene starting material).

I claim:

1. A process for preparing a cyclobutenohaloarene comprising the steps of:
   (a) providing a reaction mixture comprising an organic phase and an aqueous phase, the organic phase comprising a cyclobutenoarene;
   (b) contacting in the organic phase the cyclobutenoarene and a halogen source, said halogen source selected from sources of chlorine and bromine, under reaction conditions effective for producing a reaction product comprising the cyclobutenohaloarene and hydrogen halide and for permitting migration of the halogen halide into the aqueous phase; and
   (c) recovering the cyclobutenohaloarene from the organic phase.

2. The process of claim 1 in which the weight ratio of the aqueous phase to the cyclobutenoarene is within the range of about 0.1:1 to about 10:1.

3. The process of claim 1 in which the reaction of the cyclobutenoarene and the halogen source is effected in the absence of an acid reaction solvent for the cyclobutenoarene.

4. The process of claim 1 in which the cyclobutenoarene is benzocyclobutene.

5. The process of claim 4 which further comprises the step of separating the organic phase containing the cyclobutenohaloarene from the aqueous phase containing the hydrogen halide.

6. The process of claim 4 in which the aqueous phase comprises a chemical buffer.

7. The process of claim 4 in which the halogen source is $X_2$, wherein X is selected from the group consisting of chlorine and bromine.

8. The process of claim 1 in which the halogen source is prepared by the in situ reaction of HX, wherein X is selected from the group consisting of chlorine and bromine, and an oxidizing agent.

9. The process of claim 4 in which the weight ratio of the aqueous phase to the benzocyclobutene is within the range of from about 0.1:1 to about 10:1.

10. The process of claim 4 in which the halogen source is $Br_2$.

11. The process of claim 4 in which the halogenation reaction is carried out at a temperature within the range of about −80° C. to about 80° C.

12. The process of claim 7 in which the $X_2$ is present in the reaction mixture in an amount within the range of about 0.5 to about 1.5 moles per mole of benzocyclobutene.

13. The process of claim 1 in which the cyclobutenohaloarene is 4-bromobenzocyclobutene and the cyclobutenoarene is benzocyclobutene.

14. The process of claim 13 in which the reaction of the benzocyclobutene and the halogen source is effected in the absence of an acid reaction solvent for the benzocyclobutene and in the absence of an iodine catalyst.

15. The process of claim 14 in which the weight ratio of the organic phase to the benzocyclobutene is within the range of about 0.5:1 to about 1.5:1.

16. The process of claim 14 in which the halogenation reaction is carried out at a temperature within the range of about −20° C. to about 30° C.

17. The process of claim 16 in which the halogenation reaction is carried out over a time within the range of about 2 to about 18 hours.

18. The process of claim 14 in which the aqueous phase comprises a chemical buffer selected from the group consisting of sodium phosphates and sodium sulfates.

* * * * *